United States Patent
Yoshida et al.

(10) Patent No.: US 8,188,437 B2
(45) Date of Patent: May 29, 2012

(54) RADIATION DETECTING METHOD UTILIZING ENERGY INFORMATION AND POSITIONAL INFORMATION AND EQUIPMENT THEREOF

(75) Inventors: Eiji Yoshida, Chiba (JP); Kengo Shibuya, Chiba (JP); Taiga Yamaya, Chiba (JP); Hideo Murayama, Chiba (JP); Keishi Kitamura, Kyoto (JP)

(73) Assignees: National Institute of Radiological Sciences, Chiba-shi (JP); Shimadzu Corporation, Kyoto-shi (JP)

( * ) Notice: Subject to any disclaimer, the term of this patent is extended or adjusted under 35 U.S.C. 154(b) by 335 days.

(21) Appl. No.: 12/450,529

(22) PCT Filed: Aug. 30, 2007

(86) PCT No.: PCT/JP2007/066940
§ 371 (c)(1),
(2), (4) Date: Sep. 29, 2009

(87) PCT Pub. No.: WO2008/136141
PCT Pub. Date: Nov. 13, 2008

(65) Prior Publication Data
US 2010/0032574 A1    Feb. 11, 2010

(30) Foreign Application Priority Data
Apr. 23, 2007   (JP) ................. 2007-112925

(51) Int. Cl.
G01T 1/166 (2006.01)
(52) U.S. Cl. ................................ 250/363.04
(58) Field of Classification Search .............. 250/266, 250/269.3, 269.6, 361 R, 362, 367, 369, 363.03, 250/363.04, 363.07
See application file for complete search history.

(56) References Cited

FOREIGN PATENT DOCUMENTS
JP    A-62-203078    9/1987
JP    A-2004-279057    10/2004

OTHER PUBLICATIONS

Murayama et al., "Design of a Depth of Interaction Detector with a PS-PMT for PET," IEEE Transactions on Nuclear Science, vol. 47, No. 3, pp. 1045-1050, 2000.
Muehllehner, "Positron Camera with Extended Counting Rate Capability," Journal of Nuclear Medicine., vol. 16, No. 7, pp. 653-657, 1975.
Yoshida et al., "Energy spectra analysis of four-layer DOI detector for brain PET scanner: jPET-D4," Nuclear Instruments and Methods in Physics Research A, vol. 577, pp. 664-669, 2006.

*Primary Examiner* — Mark R Gaworecki
(74) *Attorney, Agent, or Firm* — Oliff & Berridge, PLC

(57) ABSTRACT

Upon detection of radiation by using a (three-dimensional) detector capable of distinguishing a detection position in a depth direction and energy, an energy window for distinguishing between a signal and noise is changed depending on the detection position in the depth direction, thus making it possible to obtain scattering components inside the detector. Alternatively, a weight is given to a detection event depending on the detection position in the depth direction and energy information to obtain scattering components inside the detector. Thereby, scattering components inside the detector can be obtained to increase the sensitivity of the detector. In this case, different detecting elements can be used depending on the detection position in the depth direction.

15 Claims, 12 Drawing Sheets

(A) Interactions with gamma rays (B) Energy spectrum by each interaction (C) Whole energy spectrum Depth direction (A) Energy spectrum of true coincidence (B) Energy spectrum of scatter coincidence (A) Sensitivity (B) Scatter fraction

RADIATION DETECTING METHOD UTILIZING ENERGY INFORMATION AND POSITIONAL INFORMATION AND EQUIPMENT THEREOF

TECHNICAL FIELD

The present invention relates to a radiation detecting method and equipment thereof, and in particular to a radiation detecting method utilizing energy information and positional information preferably used in positron imaging equipment or positron emission tomography (PET) equipment and to the equipment thereof.

BACKGROUND ART

As shown in FIG. 1, PET equipment is known in which positrons emitted from a positron emission nuclide 8 by the decay of +β undergo pair annihilation with surrounding electrons, and thus generated annihilation radiations 8a, 8b at 511 keV are determined by a pair of radiation detectors 10a, 10b according to the principle of coincidence. In this case, since only the annihilation radiations to which energy at 511 keV has been imparted are utilized, energy (signal) to be obtained is restricted for a lower limit and an upper limit by an energy window. Thereby, the position at which the nuclide 8 is present can be localized on one line segment connecting between the pair of detectors 10a, 10b (coincidence line: line-of-response: LOR). When an axis from the head of a body under testing to the feet is defined as a body axis, a distribution of the nuclide on a planar surface intersecting perpendicularly with the body axis is obtained by image reconfiguration in two-dimensional mode from data of the coincidence line determined on the planar surface in various directions.

A PET detector 10 is a collection of micro-detecting elements, the cross section of which is approximately 5 mm by 5 mm, and requires approximately 2 cm to 3 cm in thickness in order to detect at high probability a pair of annihilation radiations 8a, 8b oppositely emitted from the body. Further, in order to capture the pair of annihilation radiations, the detectors 10 are in general arranged in a ring shape so as to cover a subject, as shown in FIG. 2. However, radiation which is made incident obliquely into the detector 10 will cause a measurement error so as to deteriorate spatial resolution, for which there is no choice but to make the diameter of a ring much larger than the visual field.

In PET equipment, in order to acquire a higher detectability, a three-dimensional detector has been developed for detecting a depth position as well at which the radiation is made incident into a detecting element. As exemplified in FIG. 3, detecting elements of the same type 21 to 24 are stacked on a light receiving element 26, and an optical reflector placed between the detecting elements is used to control the path of light, thus making it possible to localize a depth detecting position and energy from a difference in signals output from the light receiving element 26 (refer to Japanese Published Unexamined Patent Application No. 2004-279057 (Patent Document 1), H. Murayama, H. Ishibashi, H. Uchida, T. Omura, T. Yamashita, "Design of a depth of interaction detector with a PS-PMT for PET," IEEE Trans. Nucl. Sci., Vol. 47, No. 3, 1045-1050, 2000 (Non-patent Document 1)). Further, two layers are identified for depth in general by stacking two types of detecting elements for each layer to localize a depth detecting position from a time difference in signals output from the light receiving element 26.

The above-described three-dimensional detector 20 is able to improve the deterioration of spatial resolution resulting from radiation made incident obliquely into the detecting elements. Further, the detector 20 can be brought closer to a body under testing than a detector used in the conventional PET equipment, thereby performing detection at a higher sensitivity.

On the other hand, as a method for improving the sensitivity, there is presented an idea of utilizing detector scattering shown in FIG. 4(A). In a conventional two-dimensional detector 10, as shown in FIGS. 4(B) and (C), the detector scattering cannot be distinguished from scattering from a body under testing (also referred to as a scatterer) 6. Therefore, as shown in FIG. 5 and FIG. 6, a lower limit of an energy window is adjusted to that of energy at photoelectric absorption A, by which both scattering events are eliminated as noises.

It is noted that, as shown in FIG. 7, a shield 12 for removing low-energy scattered radiation is installed on the upper face of the detector 10, thus making it possible to remove scattered radiation from the body under testing 6. However, the shield also removes partially a photoelectric absorption event (refer to G. Muehllehner: "Positron camera with extended counting rate capability," J. Nucl. Med. Vol. 16, 663-657, 1975 (Non-Patent Document 2)).

Thus, PET equipment on which three-dimensional detectors are mounted is able to adopt an arrangement of the detectors so as to give a higher sensitivity than the conventional PET equipment. Nevertheless, there is a disadvantage that a high sensitivity measurement method and a great amount of information that the PET equipment has in principle are not yet utilized to a full extent.

DISCLOSURE OF THE INVENTION

The present invention has been made in order to solve the above disadvantage, an object of which is to obtain scattering components inside a detector which would be otherwise discarded, thereby improving the sensitivity of detection.

An event scattered in the body of a subject undergoes energy loss before being made incident into a detector, and as the event is decreased in energy more greatly than 511 keV at the time when the event is made incident into the detector, there is a higher probability that the event may impart all the energy on an upper layer of the detector and halt. On the other hand, an event scattered only at a detecting element has 511 keV in energy at the time when the event is made incident, and scattered inside a crystal once or scattered repeatedly a plurality of times. Thereafter, the event will finally impart all the energy at 511 keV or will impart some of the energy and escape outside the detector, with the remaining energy retained. Where the event does not scatter in the body but imparts all the energy at 511 keV to a detecting element, the event is detected inside an energy window shown in FIG. 5. However, where the event imparts only some of the energy, the event may be out of the energy window despite the fact that it has useful positional information. Therefore, in the conventional PET equipment, as shown in FIG. 4, a true coincidence B scattered inside a detector or a scatter coincidence C cannot be identified, whereby the coincidence B having useful positional information for the most part has been discarded.

As shown in FIG. 8, since the three-dimensional detector 20 is able to reduce scattering from a scatterer (scatter coincidence) C at detecting elements on a lower layer, the detector 20 is able to utilize as a coincidence the detector scattering B as well by decreasing a lower limit of the energy window to a lower limit of detector scattering energy. The present invention is to provide a method in which the above-described events are effectively utilized to improve the sensitivity of radiation detecting equipment. A ratio of detector scattering to scattering from a body under testing is expected to be different depending on the depth at which radiation is detected and energy imparted. Therefore, if a detection position in a depth direction detected by a three-dimensional detector and energy information can be obtained, it is possible to obtain scattering components inside the detector at a region excluding that large in scattering components from a body under testing. Further, when a detection position in a depth direction detected by the three-dimensional detector and energy information are obtained, energy large in scattering components from the body under testing is decreased in weight and energy few in scattering components from the body under testing is increased in weight to acquire data, thus making it possible to obtain scattering components inside the detector, while a mixture ratio of scattering components from the body under testing is minimized.

The present invention has been made, with attention given to the above description, and has solved the problem by procedures in which upon detection of radiation by using a detector capable of distinguishing a detection position in a depth direction and energy, an energy window for distinguishing between a signal and noise is changed depending on the detection position in the depth direction, thus making it possible to obtain scattering components inside the detector.

Further, the present invention is to provide radiation detecting equipment which detects radiation by using a detector capable of distinguishing a detection position in a depth direction and energy, and the radiation detecting equipment utilizing energy information and positional information in which an energy window for distinguishing between a signal and noise is changed depending on a detection position in a depth direction, thus making it possible to obtain scattering components inside the detector.

In this case, the present invention is able to provide different detecting elements depending on a detection position in a depth direction.

The present invention has solved the above problem by procedures in which upon detection of radiation by using a three-dimensional detector capable of distinguishing a detection position in a depth direction and energy, a weight is given to a detection event depending on the detection position in the depth direction and energy information, thus making it possible to obtain scattering components inside a detector.

According to the present invention, scattering components inside a detector can be obtained to increase the sensitivity of the detector. Thereby, PET equipment, positron imaging equipment and others can be increased in sensitivity.

Further, a weight is given to a detection event depending on a detection position in a depth direction and energy information to utilize more detailed energy information, by which a mixture ratio of scattering from an object (scatterer) is reduced to utilize a detector scattering event and improve a signal to noise ratio.

BEST MODE FOR CARRYING OUT THE INVENTION

Figure 1:
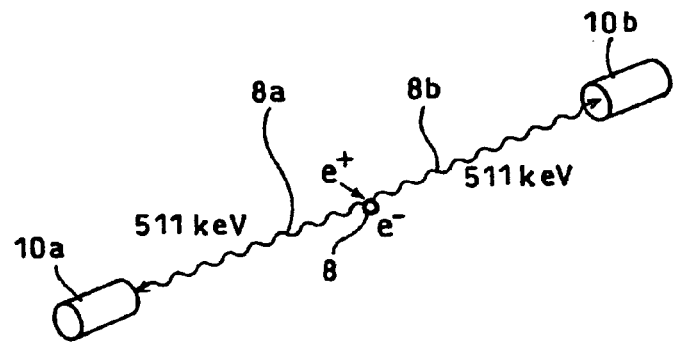
FIG. 1 is a view showing a principle of PET equipment.
Figure 2:
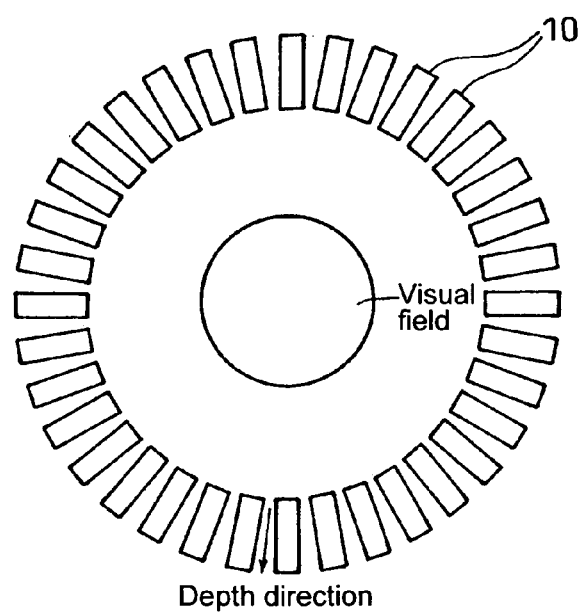
FIG. 2 is a view showing a whole constitution of the conventional PET equipment.

Hereinafter, a description will be given in detail for embodiments of the present invention by referring to the drawings.

Figure 9:
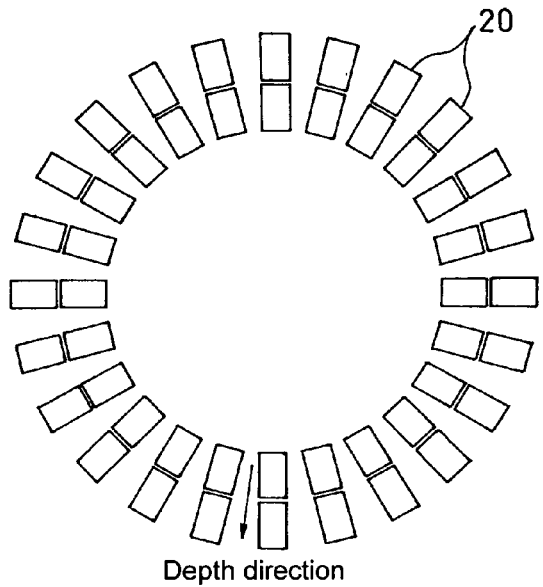
FIG. 9 is a view showing a first embodiment of PET equipment in which the present invention is utilized.
Figure 10:
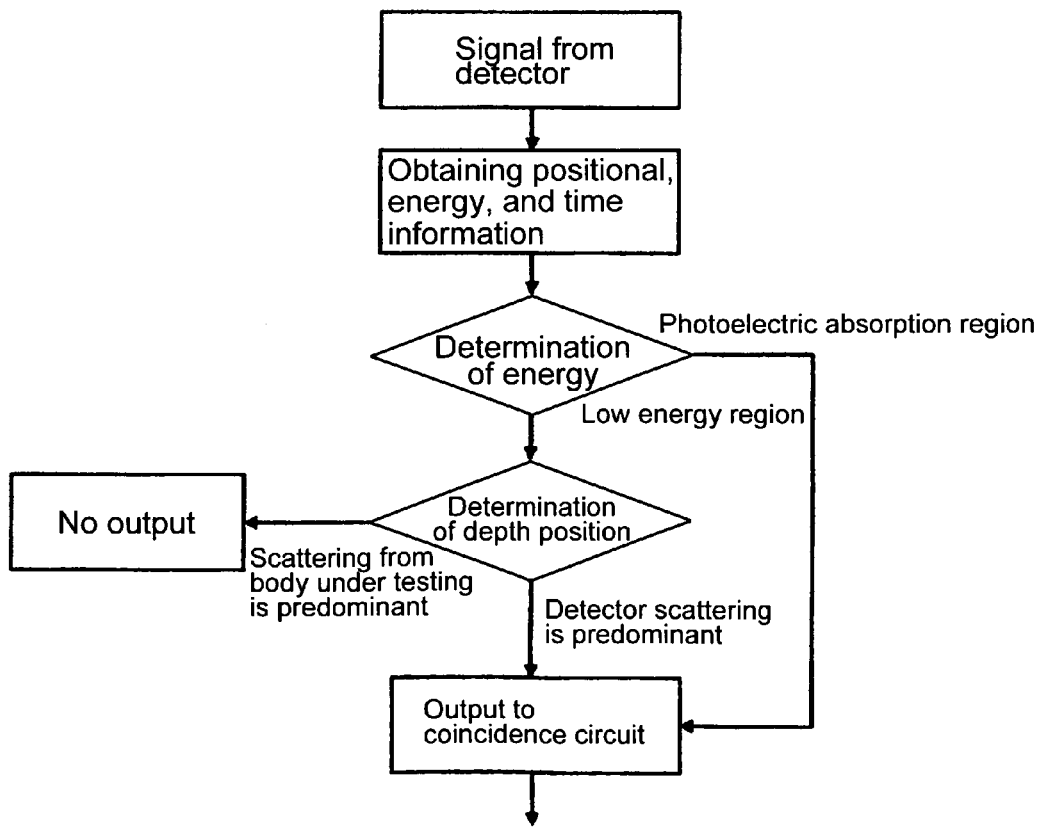
FIG. 10 is a flow chart showing data processing procedures of the first embodiment.
Figure 11:
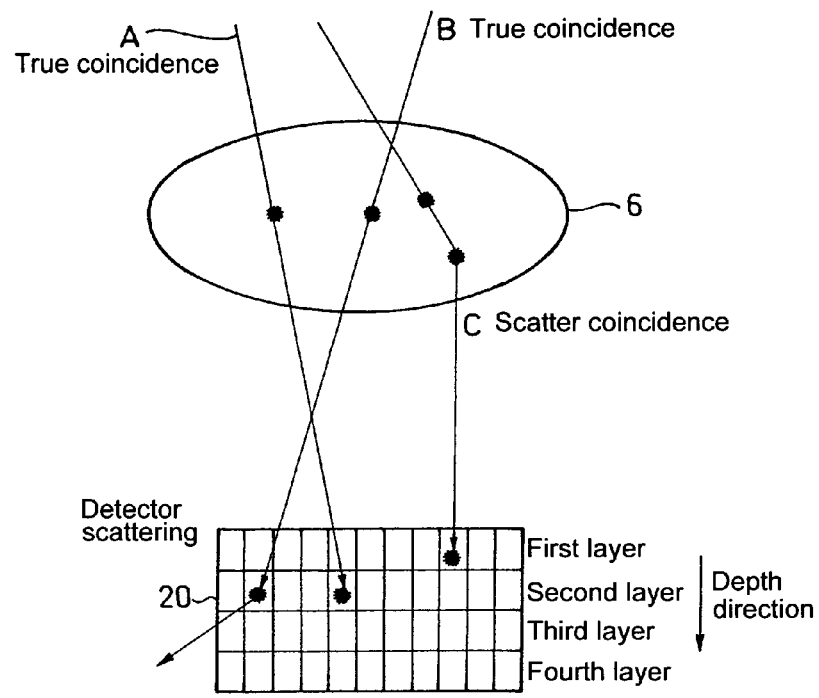
FIG. 11 is a view showing a state of radiation made incident of the first embodiment.

A first embodiment of the present invention is PET equipment or the like on which, as shown in FIG. 9, a three-dimensional detector 20 is mounted, and the PET equipment in which, as shown in FIG. 10, a detection depth is limited at a lower energy region as well to utilize detector scattering and, as shown in FIG. 11, a mechanism is provided for distinguishing between an event C scattered inside a body under testing 6 and an event B which imparts a portion of energy to the detector 20 after scattering inside the detector 20. Thereby, the PET equipment or the like having a three-dimensional detector can be further increased in sensitivity, while the deterioration of positional information is prevented.

Figure 12:
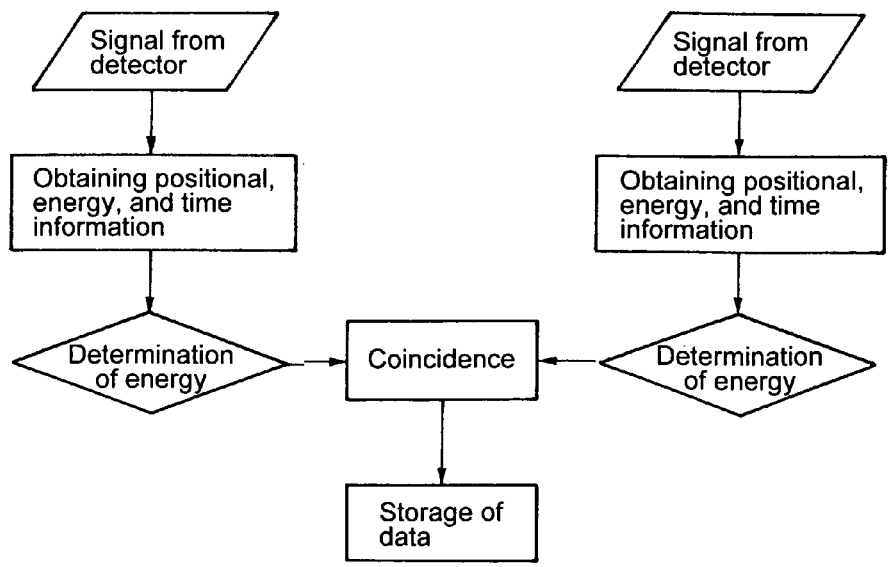
FIG. 12 is a flow chart showing coincidence procedures of the first embodiment.

FIG. 12 shows procedures of coincidence.

Figure 13:
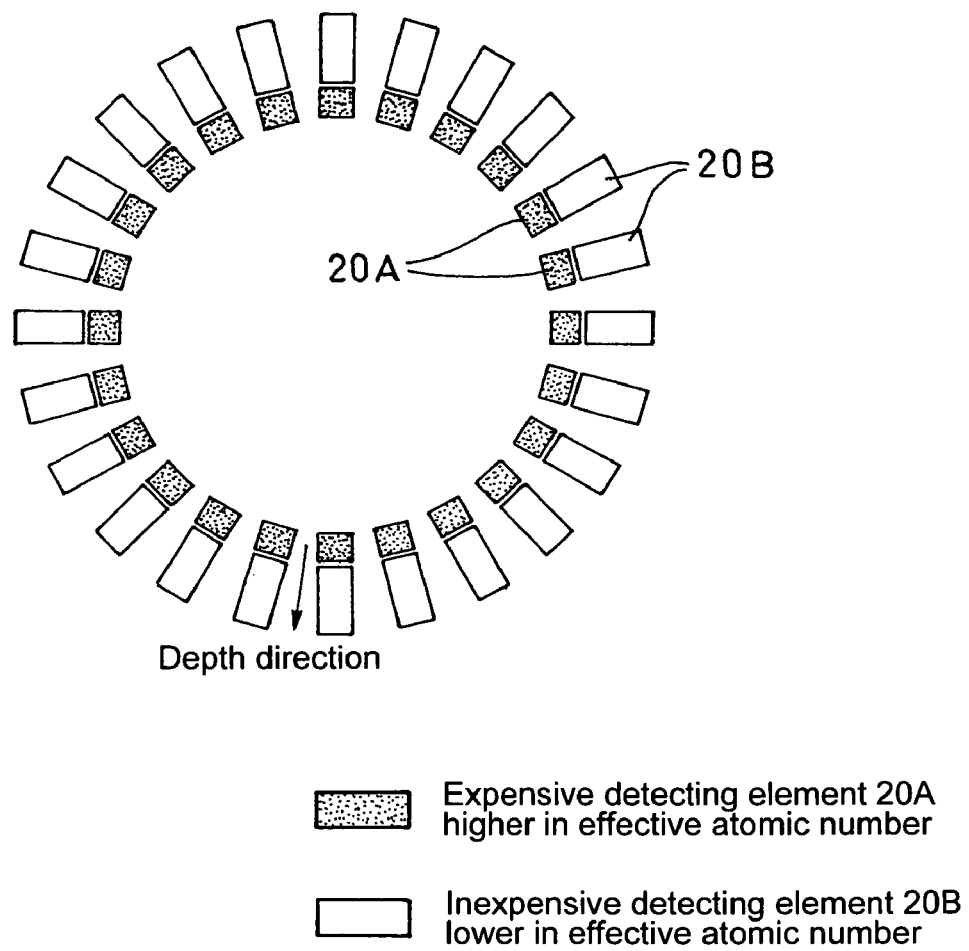
FIG. 13 is a view showing a second embodiment of the PET equipment utilizing the present invention.

Further, in the present invention, the need is eliminated for using detecting elements of the same type on all layers when the detecting elements are stacked. As described in the second embodiment shown in FIG. 13, an inexpensive detecting element 20B lower in effective atomic number is used on a lower layer unlike on an upper layer which requires an expensive detecting element 20A higher in effective atomic number, thus making it possible to use different types of detecting elements. In this case, the detecting element 20A on the upper layer is made long enough in length to stop scattered radiation but made shorter in length than the detecting element 20B on the lower layer, thereby realizing PET equipment lower in cost but higher in performance.

Alternatively, it is possible to increase the sensitivity of PET equipment in which only detecting elements lower in effective atomic number such as semiconductor detectors are used.

Figure 14:
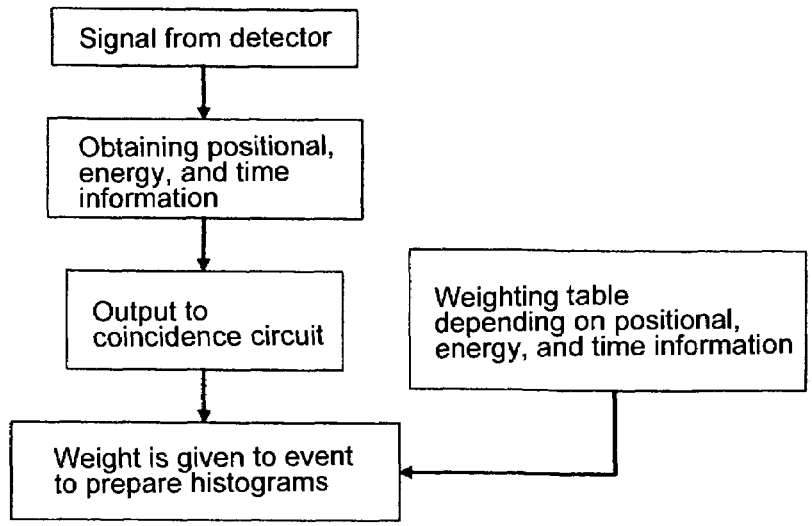
FIG. 14 is also a flow chart showing processing procedures of a third embodiment.

A third embodiment of the present invention is PET equipment or the like on which, as shown in FIG. 9, a three-dimensional detector 20 is mounted, and in which as shown in FIG. 14, a weight is given to a detection event depending on a detection position and energy, thereby acquiring histograms.

Figure 15:
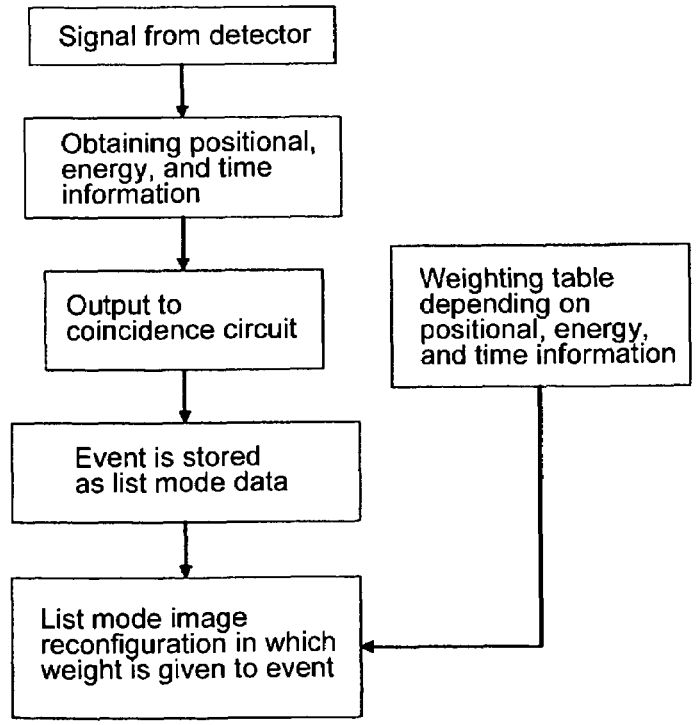
FIG. 15 is also a flow chart showing processing procedures in a fourth embodiment.

Further, as shown in FIG. 15, a fourth embodiment is that in which a detection event is stored as list mode data and, on image reconfiguration, a weight is given to a detection position and energy, thereby performing the reconfiguration.

Figure 8:
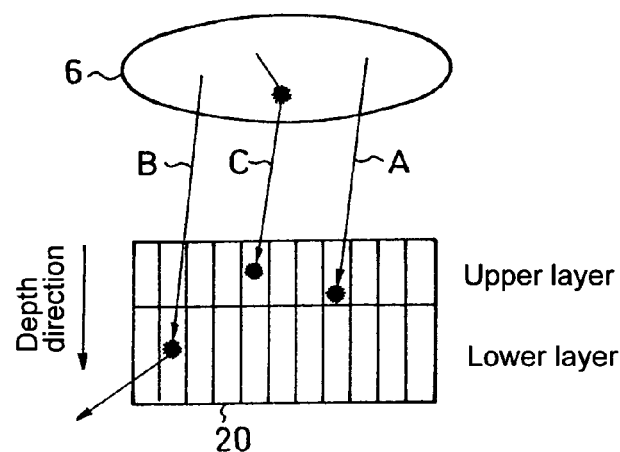
FIG. 8 is a view showing the principle of the present invention.
Figure 8:
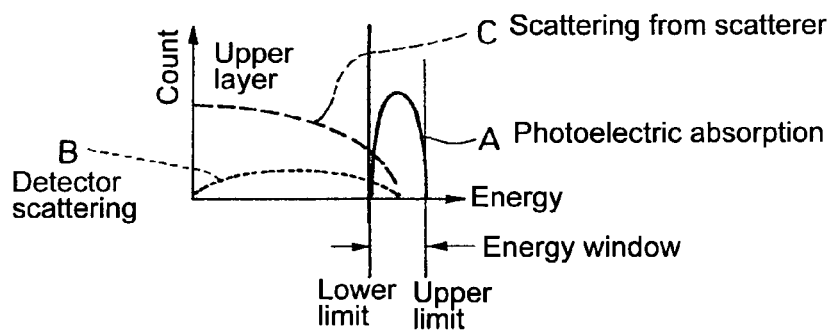
Figure 8:
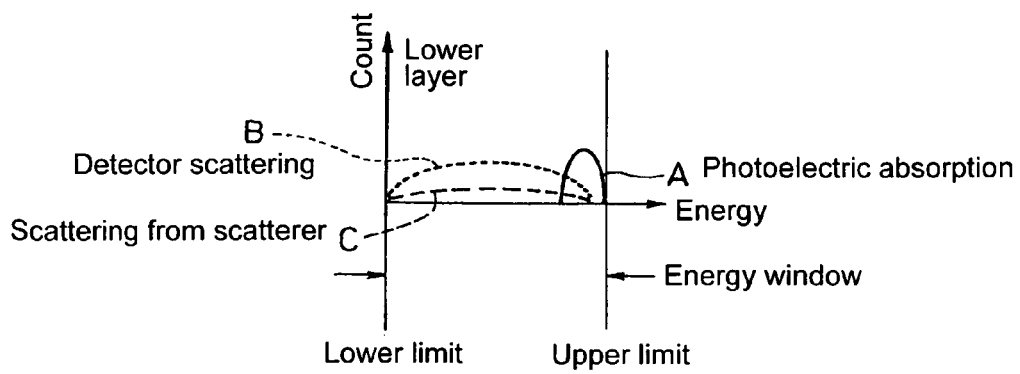

In this case, as shown in FIG. 8, a ratio of detector scattering to scattering from a scatterer at a low energy region is calculated in advance by simulation or the like, thereby tabulating a weighting depending on a detection depth (layer) and energy. The weight is set in proportion to a ratio of detector scattering to scattering from a scatterer, for example. Alternatively, in a case where a ratio of detector scattering to scattering from a scatterer is in excess of a predetermined value, calculation is made by setting the ratio to 1.0. In other cases, the calculation is made by setting the ratio to 0.0.

As described in the third and fourth embodiments, more detailed energy information is utilized than in the first or second embodiment, by which a mixture ratio of scattering from an object (scatterer) is reduced to effectively use a detector scattering event and also to improve a signal to noise ratio.

A simulation was performed by using the test model of PET equipment for the head developed by the applicant and others "jPET-D4" (refer to E. Yoshida, K. Kitamura, T. Tsuda, et. al.: "Energy spectra analysis of four-layer DOI detector for brain PET scanner: jPET-D4," Nucl. Instr. Meth. A, 577, 664-669, 2006 (Non-Patent Document 3). In this equipment, three-dimensional detectors 20 each of which is made up of four stacked layers of a GSO scintillator measuring 2.9 mm×2.9 mm×7.5 mm were used to constitute a detector ring measuring 39 cm in ring diameter and 26 cm in length. As a phantom simulating a body under testing 6, a cylindrical phantom measuring 20 cm in diameter and 20 cm in length was filled with water and a pair of 20 cm-across linear radiation sources which emit a pair of radiation at 511 keV were installed on the central axis.

Figure 16:
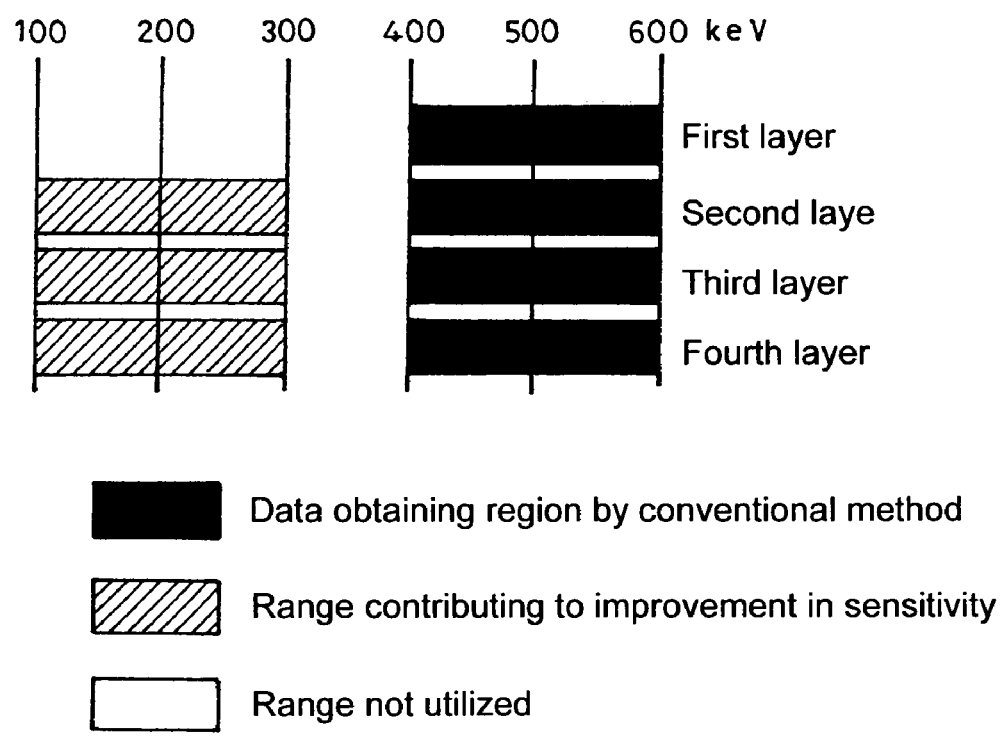
FIG. 16 is a view showing an energy window of the embodiments.

In a conventional method, energy windows are the same on all layers, for example, 400 to 600 keV. However, in a method according to the present invention, as shown in FIG. 16, an energy window from 400 to 600 keV was provided on a first layer, while two energy windows from 100 to 300 keV and 400 to 600 keV were provided on a second to a fourth layer. More specifically, provided was an energy window from 100 to 600 keV excluding a range from 300 to 400 keV. As described above, a plurality of energy windows may be installed whenever necessary, which is different from the conventional PET equipment.

Figure 17:
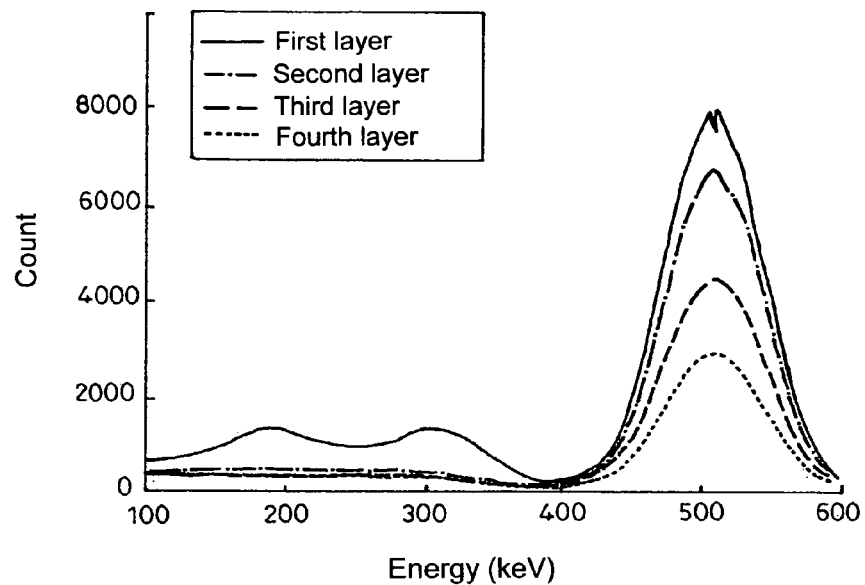
FIG. 17 is a view showing an energy spectrum of (A) true coincidence and that of (B) scattered coincidence in a comparative manner.
Figure 17:
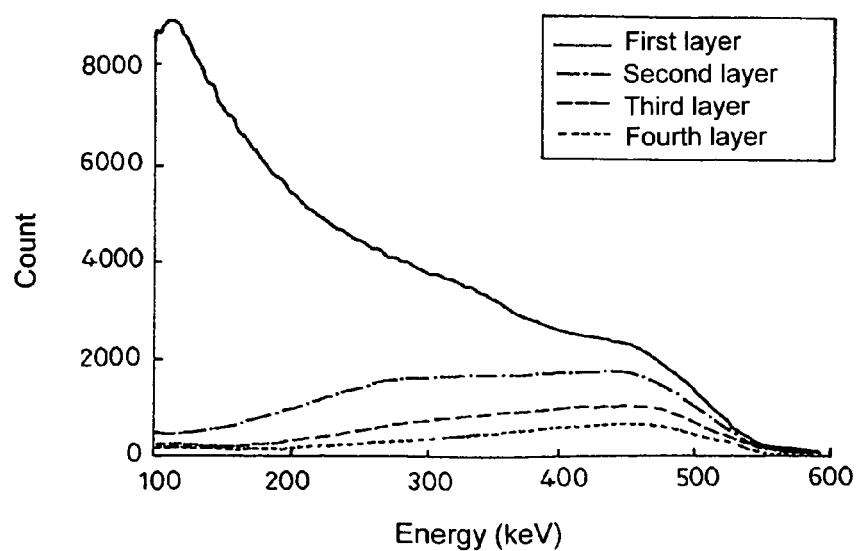

FIG. 17 shows an energy spectrum of (A) true coincidence and that of (B) scatter coincidence. It is apparent that as the layer goes further down, influence of scattered radiation from a body under testing shown in (B) is reduced.

Figure 18:
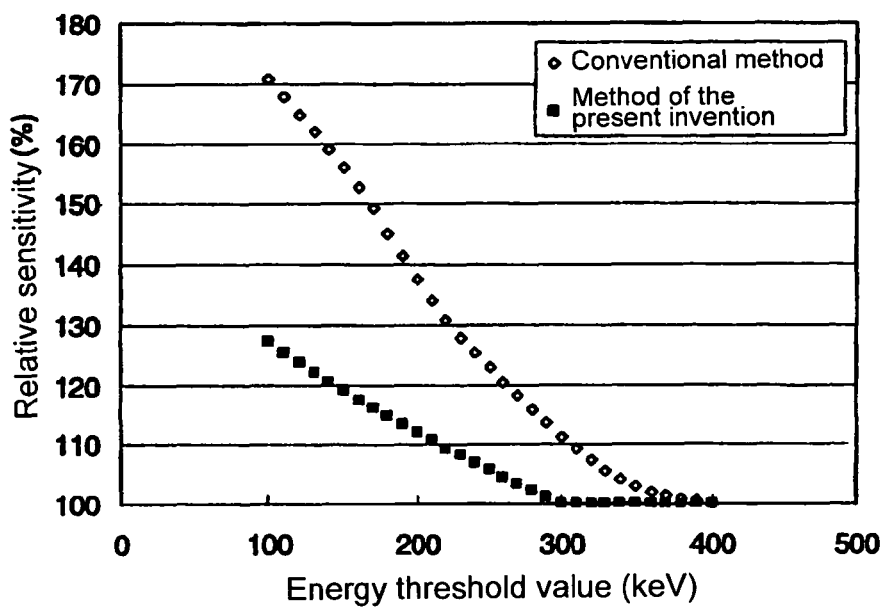
FIG. 18 is also a view showing (A) sensitivity and (B) scatter fraction in a comparative manner.
Figure 18:
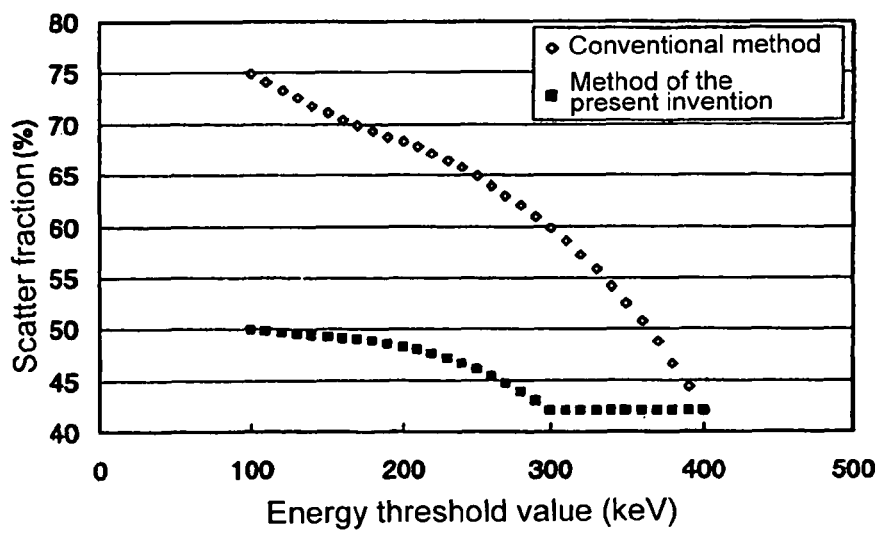

FIG. 18 shows a change in (A) relative sensitivity and (B) scatter fraction (ratio at which object scattering is contained in measured data) when the lower limit of an energy window is changed. In the relative sensitivity, the lower limit 400 keV of the energy window is given as 100. As apparent from this drawing, the present invention is able to provide a higher sensitivity while suppressing an increase in scatter fraction.

Figure 3:
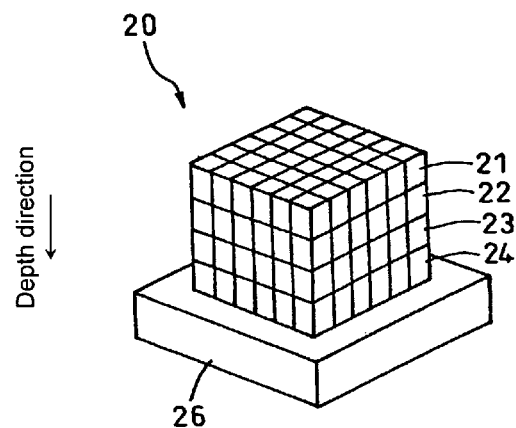
FIG. 3 is a perspective view showing a three-dimensional detector presented in Patent Document 1.
Figure 4:
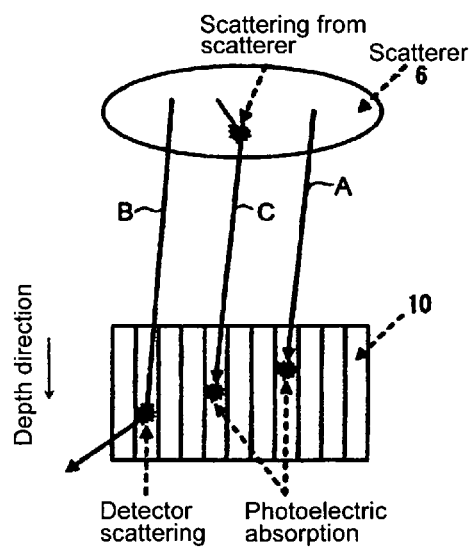
FIG. 4 is a view showing interactions of gamma rays and energy spectrum for describing a principle of the present invention.
Figure 4:
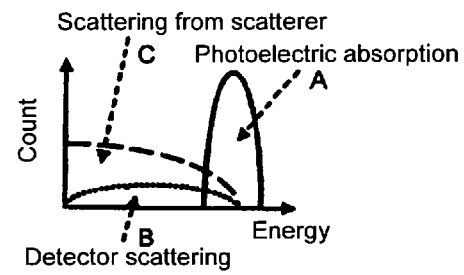
Figure 4:
Figure 5:
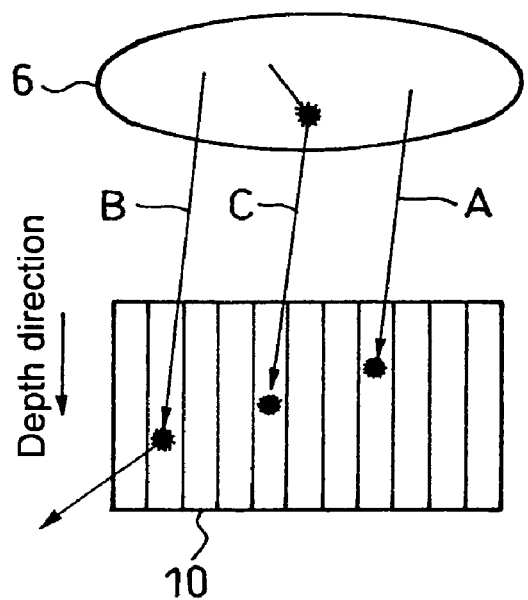
FIG. 5 is a view showing a method for removing scattered radiation by a conventional energy window.
Figure 5:
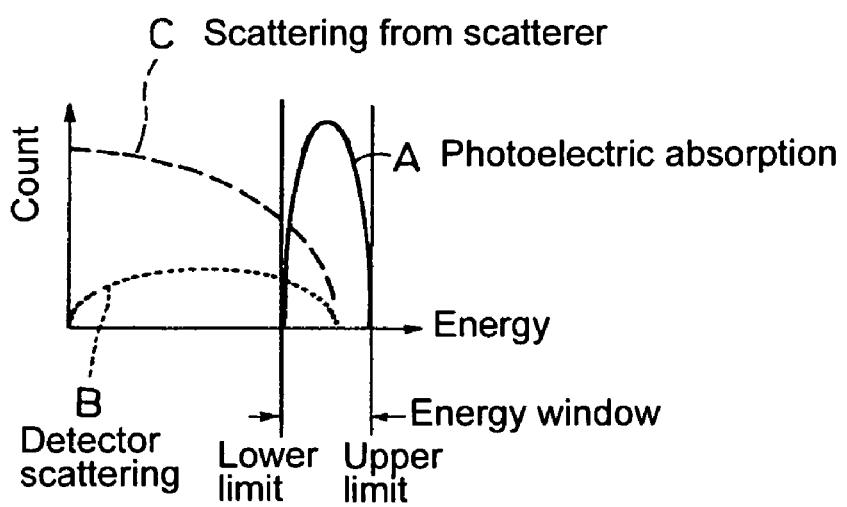
Figure 6:
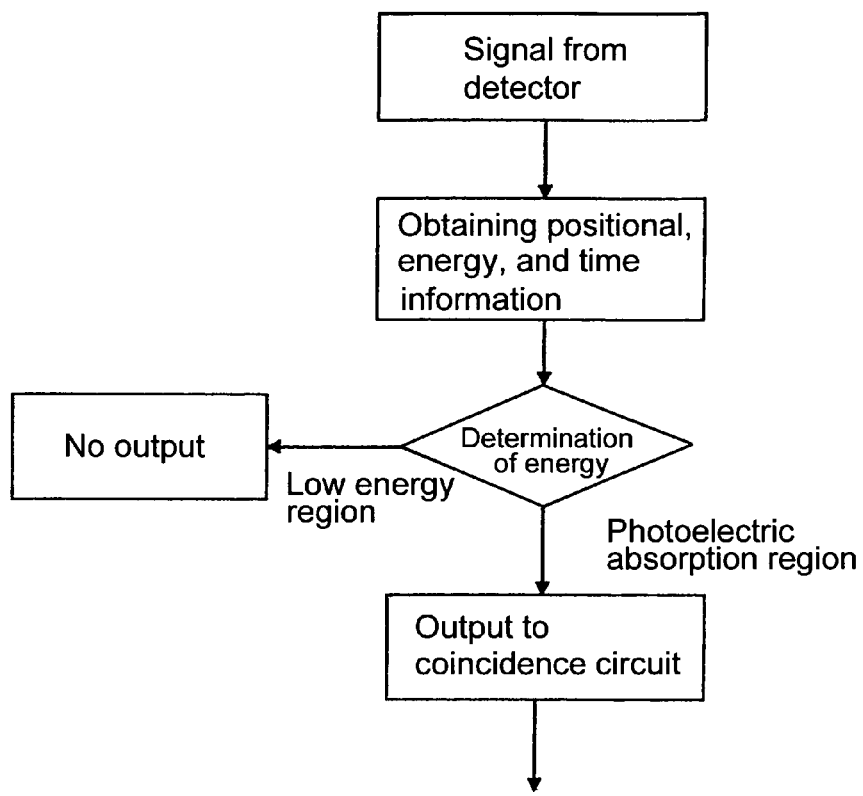
FIG. 6 is a view showing data processing by a conventional method.
Figure 7:
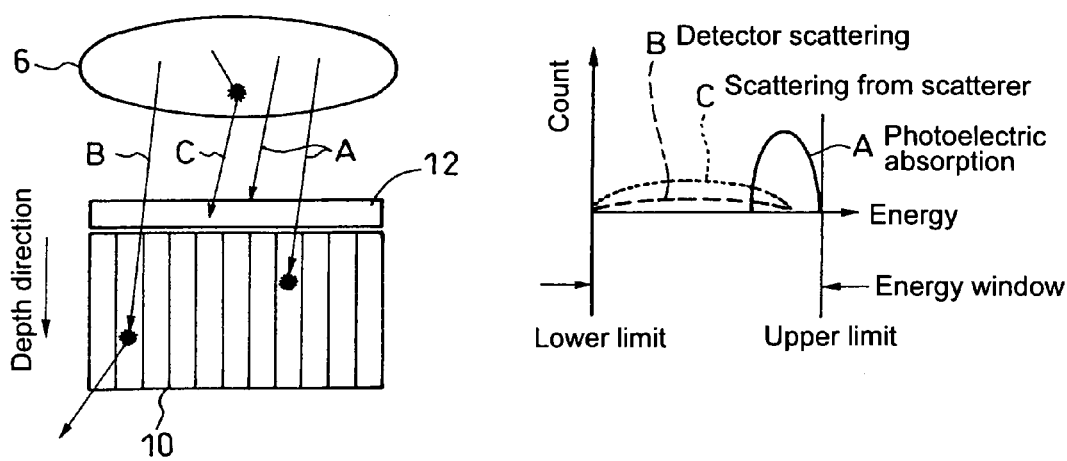
FIG. 7 is a view showing a method for removing scattered radiation by a conventional shield.

In the previous description, the present invention is applied to PET equipment. However, the present invention shall not be limited thereto but may be applied to other nuclear medical imaging equipment such as positron imaging equipment and also to radiation detecting equipment in general. Further, the three-dimensional detector shall not be limited to the type shown in FIG. 3 and also acceptable is that which is able to distinguish a position in a depth direction in an analog manner.

INDUSTRIAL APPLICABILITY

The present invention is applicable to nuclear medical imaging equipment such as positron imaging equipment and also to radiation detecting equipment in general, in addition to PET equipment.

What is claimed is:

1. A radiation detecting method utilizing energy information and positional information, comprising the steps of:
   detecting radiation by using a detector adapted to distinguish a detection position of energy in a depth direction of the detector, the detector changing a width of an energy window for distinguishing between a signal or noise depending on the detection position of the energy in the depth direction of the detector, by utilizing information on detection of radiation having a small number of scattering components using two or more widths of the energy windows for single-energy radiation, depending on a detection position in a depth direction of the detector, and
   obtaining scattering components inside the detector.

2. The radiation detecting method according to claim 1, wherein
   different detecting elements are provided depending on a detection position in a depth direction of the detector.

3. The radiation detecting method according to claim 1, wherein
   a weight is given to a detection event depending on the detection position in the depth direction of the detector and energy information.

4. Radiation detecting equipment which detects radiation by using a detector adapted to distinguish a detection position of energy in a depth direction of the detector, the radiation detecting equipment utilizing energy information and positional information, wherein
   the detector changes a width of an energy window for distinguishing between a signal and noise is changed depending on a detection position of the energy in a depth direction of the detector, and
   information on detection of radiation having a small number of scattering components using two or more widths of energy windows is utilized for single-energy radiation, depending on a detection position in a depth direction of the detector, thus making it possible to obtain scattering components inside the detector.

5. The radiation detecting equipment according to claim 4, wherein
   a lower limit of the energy window of the lower layer detecting element is set to a lower limit of detector scattering energy.

6. The radiation detecting equipment according to claim 4, wherein
   different detecting elements are provided depending on a detection position in a depth direction of the detector.

7. The radiation detecting equipment according to claim 4, wherein
a weight is given to a detection event depending on the detection position in the depth direction of the detector and the energy information.

8. A radiation detecting method utilizing energy information and positional information, comprising the steps of:
detecting radiation by using a detector having stacked detecting elements of two or more layers including a lower layer detecting element and a higher layer detecting element, and the detector adapted to distinguish a detection position of energy in a depth direction of the detector, with a width of an energy window for distinguishing between a signal or noise of the lower layer detecting element being wider than the energy window of the higher layer detecting element, and
obtaining scattering components inside the detector.

9. The radiation detecting method utilizing energy information and positional information according to claim 8, wherein
a lower limit of the energy window of the lower layer detecting element is set to a lower limit of detector scattering energy.

10. The radiation detecting method according to claim 8, wherein
different detecting elements are provided depending on a detection position in a depth direction of the detector.

11. The radiation detecting method according to claim 8, wherein
a weight is given to a detection event depending on the detection position in the depth direction of the detector and energy information.

12. Radiation detecting equipment which detects radiation by using a detector adapted to distinguish a detection position of energy in a depth direction of the detector, the radiation detecting equipment utilizing energy information and positional information, wherein
the detector changes a width of an energy window for distinguishing between a signal and noise depending on a detection position in a depth direction, of the detector, thus making it possible to obtain scattering components inside the detector,
the detector has two or more detector layers including a lower layer detecting element and an upper layer detecting element, and
an energy window for distinguishing between a signal or noise of the lower layer detecting element is made wider than the energy window of the higher layer detecting element.

13. The radiation detecting equipment according to claim 12, wherein
a lower limit of the energy window of the lower layer detecting element is set to a lower limit of detector scattering energy.

14. The radiation detecting equipment according to claim 12, wherein
different detecting elements are provided depending on a detection position in a depth direction of the detector.

15. The radiation detecting equipment according to claim 12, wherein
a weight is given to a detection event depending on the detection position in the depth direction of the detector and the energy information.

* * * * *